United States Patent [19]

Van Pool

[11] 4,316,998
[45] Feb. 23, 1982

[54] TREATMENT OF SULFUR-CONTAINING HF-ALKYLATION FEED, HYDROCARBON PRODUCT, PROPANE AND ACID-SOLUBLE OILS DERIVED FROM THE ALKYLATION

[75] Inventor: Joe Van Pool, Bartlesville, Okla.

[73] Assignee: Phillips Petroleum Company, Bartlesville, Okla.

[21] Appl. No.: 173,304

[22] Filed: Jul. 29, 1980

[51] Int. Cl.³ .................... C07C 2/56; C07C 2/58; C07C 7/10
[52] U.S. Cl. ....................................... 585/712; 55/71; 423/241; 585/723; 585/842
[58] Field of Search ............... 585/723, 712, 842; 55/71; 423/241

[56] References Cited

U.S. PATENT DOCUMENTS

| | | | |
|---|---|---|---|
| 2,282,712 | 5/1942 | Engs et al. | 55/71 X |
| 2,288,865 | 7/1942 | Baehr et al. | 55/71 X |
| 2,371,759 | 3/1945 | King et al. | 23/88 |
| 3,886,220 | 5/1975 | Carter | 585/723 X |
| 4,123,351 | 10/1978 | Chapman et al. | 585/854 |

OTHER PUBLICATIONS

The Merck Index, 8th Ed., p. 855 (1968).

Primary Examiner—John Doll

[57] ABSTRACT

HF is removed from hydrocarbon streams, e.g., a propane liquid stream from HF alkylation by water washing, the wash stream being contacted with solid caustic to remove moisture therefrom. The used wash water containing HF is combines with aqueous caustic obtained from said contacting and the admixture is used to contact HF acid soluble oil to remove HF therefrom. The thus, used aqueous stream separated from this last contacting is reacted with a calcium compound to form insoluble calcium fluoride and a supernatant aqueous liquid containing regenerated caustic. The regenerated caustic is used to remove the sulfur compounds from the alkylation hydrocarbons feed.

8 Claims, 1 Drawing Figure

U.S. Patent Feb. 23, 1982 4,316,998
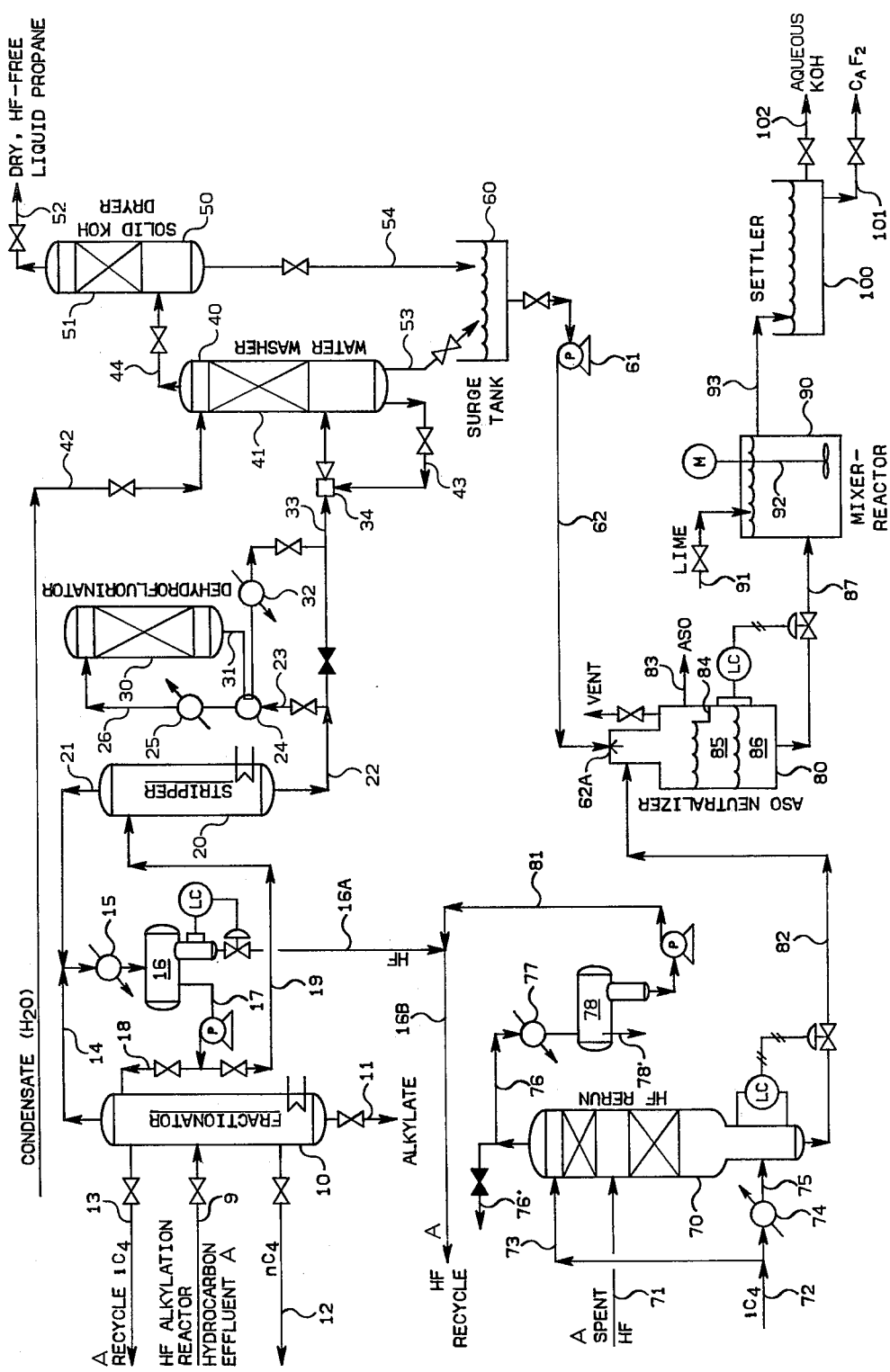

TREATMENT OF SULFUR-CONTAINING HF-ALKYLATION FEED, HYDROCARBON PRODUCT, PROPANE AND ACID-SOLUBLE OILS DERIVED FROM THE ALKYLATION

BRIEF DESCRIPTION OF INVENTION

A propane-containing stream is water washed to substantially completely remove HF therefrom. The thus-obtained stream is dried by contact with solid caustic alkali. The wash water and water containing alkali from the caustic contacting are combined and used to treat acid soluble oil to remove HF therefrom. The thus-obtained treating medium is neutralized as with lime to regenerate a caustic solution which, in one embodiment, is employed to remove sulfur-containing compounds from the olefin feed to the alkylation.

BRIEF DESCRIPTION OF DRAWING

In the drawing, there are shown a combination fractionation-stripping operation in which HF alkylation reactor hydrocarbon effluent is fractionated to remove alkylate therefrom and to obtain a stream containing propane, organic fluorides, and HF. This stream is dehydrofluorinated as in the presence of activated alumina, yielding an HF containing propane stream. The propane stream is water washed and then contacted with solid caustic alkali to dry the same. The water wash and aqueous caustic thus obtained are admixed with acid soluble oils obtained from an HF rerun operation, shown, to remove HF therefrom. Upon separation of phases the aqueous phase containing fluoride, caustic and water, is treated as with lime to produce insoluble fluoride and to regenerate caustic. The caustic is used to treat olefin-containing feed to remove sulfur containing compounds therefrom.

A DETAILED DESCRIPTION

This invention relates to alkylation. In one of its aspects, it relates to the treatment of various streams in an alkylation operation in which an isoparaffin is alkylated with an olefin. In a more specific aspect of the invention, it relates to the removal of HF, organic fluorides, as well as sulfur-containing compounds from streams in an HF alkylation of an isoparaffin with an olefin.

In one of its concepts, the invention provides a process for the treatment of a propane-containing stream, also containing HF, to substantially completely remove the HF therefrom which comprises washing the propane stream with water, preferably a condensate water. In another of its concepts, the invention provides a combination of steps for the removal of HF from a propane-containing stream, also containing HF, which comprises water washing the propane stream to substantially completely remove all of the HF therefrom and then contacting said stream with solid caustic, preferably solid potassium hydroxide pellets to dry said stream. It is important for reasons appearing herein to avoid slugs of HF in a solid caustic treating bed. The water-washed step of this invention is for said reasons an important contribution to alkylation systems using solid caustic treating. In a further concept of this invention, it provides a combination operation in which the used wash water and alkaline water resulting from the dehydration step are, preferably in combined form, used to remove fluorine compounds from acid soluble oils recovered in an HF rerun operation. In a further concept still of the invention, the recovered treating fluid, upon treatment of the acid soluble oil, is regenerated with a soluble calcium compound such as lime, to produce or to regenerate an aqueous caustic. In another concept of the invention, it provides for use of a regenerated caustic to treat an olefin containing feed to the alkylation to remove sulfur containing compounds, e.g., $H_2S$ and mercaptans therefrom.

The caustic treatment of hydrocarbon streams, e.g., propane to remove hydrogen fluoride therefrom, is known. It is also known, as shown in U.S. Pat. Nos. 4,162,272 and 4,162,273, issued July 24, 1979, to use aqueous caustic solutions to remove HF from a propane-containing stream. Further, it is known, as shown in U.S. Pat. No. 4,123,351, issued Oct. 30, 1978, to remove HF from a hydrocarbon stream by chemical reaction with solid caustic alkali, e.g., potassium hydroxide pellets. In the last-mentioned patent, according to the invention described therein, there is provided a control system and method to regulate the flow of hydrocarbons charged to the treater responsive to temperature changes within the system which indicate any excessive amount of HF in the hydrocarbon stream, thereby preventing the treater temperature from exceeding a preselected maximum allowable value. In a further concept of the invention still, there is provided an acid soluble oil treatment which comprises treating such an oil obtained from an acid rerun unit or operation with water wash fluid obtained from water washed propane containing HF and aqueous alkaline solutions obtained from a caustic dryer to remove from the acid soluble oil fluorine-containing compound, e.g., HF, therein. U.S. Pat. No. 2,614,132, issued Oct. 14, 1952, discloses the recovery of drying oils from HF-hydrocarbon complexes with an aqueous HF solution, therein defined.

The disclosures of the patents above mentioned are incorporated herein by this reference to them.

It is an object of this invention to provide an improved alkylation operation. It is a further object of this invention to remove HF from streams containing the same. It is a still further object of the invention to remove organically combined fluorine from hydrocarbons obtained in the HF alkylation of an isoparaffin with an olefin. A still further object of the invention is to provide an improved process for the alkylation of an isoparaffin with an olefin employing HF-acid catalyst. Another object of the invention is to provide a method of treating propane containing HF prior to contacting the propane with solid caustic, e.g., prior to contacting the propane with sodium hydroxide and/or potassium hydroxide pellets or particles. A further object of the invention is to provide a method for treating an acid soluble oil to remove fluorine compounds, e.g., HF, therefrom. Another object of the invention is to regenerate a caustic solution from one which has been used to remove fluorine containing compounds. A still further object of the invention is to remove the sulfur-containing compound from an olefin-containing feed to an alkylation operation in which fluorine-containing compounds are removed using a caustic material.

Other aspects, concepts, objects and the several advantages of the invention are apparent from a study of this disclosure, the drawing and the appended claims.

According to the present invention, a propane-containing stream, also containing HF, is washed with water to substantially completely remove HF therefrom. At most, only a trace of HF will remain in the propane.

Further, according to the invention, the water-washed propane now substantially completely freed of HF is contacted with solid caustic to dry the same.

Still further according to the invention, the used water and alkaline water resulting from the caustic drying step are used, preferably in combined form, to treat the acid soluble oil obtained from an HF catalyst rerun unit to remove therefrom HF.

Further according to the invention, the used treating solution now containng alkali fluoride, is regenerated to produce an aqueous alkaline (hydroxide) solution, as is shown, and the aqueous alkaline solution is used to remove sulfur containing compounds from olefin-containing feed fed to the alkylation operation.

Referring now to the drawing, an HF alkylation reactor hydrocarbon effluent is fed by 9 to fractionator 10. Normal butane and recycle isobutane, to be recycled to the alkylation operation, are taken off at 12 and 13 respectively. Alkylate is withdrawn at 11. Fractionator overhead 14 is cooled and condensed in condenser 15 and accumulated as well as phase-separated in accumulator 16 from which a pump recycles hydrocarbon phase by 17 and 18 through the fractionator as liquid reflux therefor. An acid leg is provided on which a level control to remove substantially only liquid HF acid by 16A and 16B for recycle to the alkylation operation, designated as A, not shown. Also removed from accumulator 16 and passed by 19 to stripper 20 is hydrocarbon phase to be stripped in stripper 20, from which propane and acid-containing vapors are passed by 21 to condenser 15 and to accumulator 16. Bottoms from stripper 20 pass by 22, and this embodiment, for dehydrofluorination as with activated alumina, in a known manner, by 23, heat exchanger 24, steam heater 25, and 26. Bottoms are withdrawn from dehydrofluorinator 30 by 31, heat exchanged at 24, cooled at 32 and fed by 33 to eductor 34 wherein this stream, essentially comprising propane and HF, is admixed with wash water drawn from water washer settler 40, with coalescing means 41, by 43. Water washer settler 40 is fed water, preferably condensate water, for washing the propane to substantially completely remove HF therefrom into the water. Condensate, e.g., steam condensate, is preferred since no calcium is usually present therein and insoluble salts, e.g., $CaF_2$, will not be present at this locus. Condensate water is preferred and it is a feature of this invention because it will avoid hindering of the settling which is to take place as in the acid soluble oil neutralizer 80 to be described. At most, only a detectable trace of HF will remain in the propane which passes by 44 to solid caustic, preferably pellets 51 of KOH, in dryer 50, from which there passes overhead at 52 dry, HF-free liquid propane (LPG).

Aqueous alkaline solution and wash water are taken, respectively, from the dryer 50 and the water washer 40 by way of 54 and 53, respectively, admixed in surge tank 60 and pumped by pump 61 and by 62 into a spray contactor 62a in the top of acid soluble oil neutralizer 80.

There is shown an HF rerun operation comprising essentially a rerun tower 70 from which spent HF acid catalyst, from an HF alkylation operation A, not shown, is passed at 71 and wherein it is contacted with isobutane introduced at 72, heated and vaporized at 74, and passed by 75 into HF rerun tower 70. A portion of the isobutane is fed by 73 into the top of the HF rerun tower as liquid reflux. From the top of the HF rerun tower there is taken overhead vapor at 76 HF and isobutane which has been substantially freed of acid soluble oil stream 76 is condensed at 77, accumulated at 78 and pumped therefrom by 81 and 16B as HF recycle to the alkylation operation A. Isobutane is passed by 78' to the alkylation. If desired HF and isobutane vapor 76' can be returned to the alkylation.

Returning now to acid soluble oil neutralizer 80, bottoms 82 from the HF rerun which comprise HF-containing acid soluble oil are admixed at 62A with the now combined HF-alkaline solution and the wash water from dryer 50 and water washer 40, respectively.

In the acid soluble oil neutralizer, two liquid phases are formed. A supernatant acid soluble oil liquid which has been substantially freed from residual HF to a substantial extent is removed at 83 as a product of the operation. The supernatant phase is shown at 85 and the level thereof is controlled by wier 84. The acid soluble oil liquid is removed by 83. The liquid aqueous phase 86 is removed, on interface level control, by 87 to mixer-reactor 90 wherein the aqueous phase is treated with slaked lime, $Ca(OH)_2$, introduced at 91. A mixer 92 effects contact of the lime and the aqueous alkaline solution containing alkali fluoride. From the reactor 90 the thoroughly admixed materials are passed by 93 to settler 100 from which calcium fluoride is removed by 101, and which can be discarded without harm to the ecology. Aqueous caustic, e.g., KOH, is passed by 102 and by means, not shown for the sake of simplicity, to the alkylation operation olefin-containing feed to remove therefrom sulfur containing compounds, e.g., $H_2S$, and mercaptans.

The following is a calculated example given to further set forth and to illustrate the invention to one skilled in the art.

| Stream 22 | | |
|---|---|---|
| Barrels/hour | | 709 |
| Composition | | |
| Propane, wt. % | 97.44 | |
| Organic fluoride | 200 (ppm by wt.) | |
| HF | 10 (ppm by wt.) | |
| Temperature, °F. | | 140 |
| Stream 26 | | |
| Barrels/hour | | 709 |
| Temperature, °F. | | 350 |
| Stream 33 | | |
| Barrels/hour | | 709 |
| Composition | | |
| Propane, wt. % | 97.46 | |
| Organic fluoride | 1 (ppm by wt.) | |
| HF | 3 (ppm by wt.) | |
| Temperature, °F. | | 100 |
| Stream 42 | | |
| Water, barrels/day | (8400 lbs/day) | 24 |
| Temperature, °F. | | 100 |
| Stream 44 | | |
| Barrels/hour | | 709 |
| Composition | | |
| Propane, wt. % | 94.44 | |
| Organic fluoride | nil to 1 (ppm by wt.) | |
| HF | trace | |
| Water | 360 (ppm by wt.) | |
| Temperature, °F. | | 100 |
| Stream 52 | | |
| Barrels/hour | | 709 |
| Composition | | |
| Propane, wt. % | 97.46 | |
| Organic fluoride | nil to 1 | |
| HF | nil | |
| Water ppm by wt. | 5 | |
| Temperature, °F. | | 100 |
| Stream 53 | | |
| Pounds/day | | 8354 |

-continued

| | | |
|---|---|---|
| Composition | | |
| Water, wt. % | (100) | |
| HF, ppm by wt. | 46 | |
| Temperature, °F. | | 100 |
| Stream 54 | | |
| Pounds/day | | 103.2 |
| Composition | | |
| Water, Wt. % | 44 | |
| KOH, wt. % | 56 | |
| KF | trace | |
| Temperature, °F. | | 100 |
| Stream 62 | | |
| Pounds/day | | 8457.2 |
| Composition | | |
| Water, wt. % | 99.32 | |
| KOH, wt. % | 0.68 | |
| Temperature, °F. | | 100 |
| Stream 82 | | |
| Barrels/day | (990 lbs/day) | 3 |
| Composition | | |
| Acid Soluble Oil wt. % | 98.99 | |
| HF, wt. % | 1.01 | |
| Temperature, °F. | | 350 |
| Stream 83 | | |
| Barrels/day | (980 lbs/day) | 3 |
| Composition | | |
| Acid Soluble Oil wt. % | 100 | |
| HF | nil | |
| (H$_2$O, KOH, KF) | nil | |
| Temperature, °F. | | 120 |
| Stream 87 | | |
| Pounds/day | | 8467.2 |
| Composition | | |
| Water, wt. % | 99.31 | |
| KF, wt. % | 0.34 | |
| KOH, wt. % | 0.35 | |
| Temperature, °F. | | 120 |
| Stream 91 (Ca(OH)$_2$) | | |
| Lime, lbs/day | (stoic) (c) | 18.52 |
| Stream 101 | | |
| lbs/day | | 370.45 |
| Composition | | |
| Water, wt. % | 94.48 | |
| CaF$_2$, wt. % | 4.86 | |
| KOH, wt. % | 0.66 | |
| Temperature, °F. | | 110 (a) |
| Stream 102 | | |
| Lbs/day | | 8115.67 |
| Composition | | |
| Water, wt. % | 99.25 | |
| KOH, wt. % | 0.74 | |
| Ca(OH)$_2$, wt. % | 0.01 | |
| Temperature, °F. | | 100 (a) |

| Unit Operating Conditions: | | |
|---|---|---|
| Unit No. | Temperature, °F. | Pressure, psig |
| 30 | 350 | 260 |
| 40 | 100 | 258 |
| 50 | 100 | 256 |
| 60 | 100 | atmos. |
| 80 | 120 | 1 |
| 90 | (b) 110 | atmos. |
| 100 | (b) 110 | atmos. |

(a) (Heat Loss to Atmosphere)
(b) No cooling
(c) Can use more than stoichiometric amount.

All other units are conventionally operated.

It will be appreciated by one skilled in the art in possession of this disclosure and having studied the same, that the water washing substantially completely removes the HF from the propane stream. In lieu of eductor 34 or together therewith there can be a pump interposed in line 43 to augment the contact of water with the propane stream containing HF. In any event, one skilled in the art will assure that any surge of HF will be completely absorbed in the rapidly circulating waters which are circulated in high enough volume to ensure that any foreseeable surge of HF will be totally absorbed before the propane passes to the solid caustic dryer at 50. Thus, this feature of the invention in which all detectable traces of HF are substantially completely removed from the propane is advantageously combined, also as a feature of the invention, with the solid caustic dryer.

It will be evident to one skilled in the art in possession of this disclosure, having studied the same, that he has been furnished an overall combination of the individual features of the invention which will save energy, as well as cost of operation in the overall.

Reasonable variation and modification are possible within the scope of the foregoing disclosure, drawing and the claims to the appended invention, the essence of which is that there have been set forth water washing to remove substantially completely HF from a hydrocarbon stream containing the same, e.g., a propane stream containing HF as obtained in an alkylation operation; a solid caustic contacting in combination with such a water washing; a treatment of acid soluble oil with used water from the water wash and aqueous alkaline solution obtained from the solid caustic drying; the regeneration and use of regenerated aqueous alkaline caustic solution for removal of sulfur containing compounds from olefin-containing feed fed to the alkylation operation.

I claim:

1. A process for the alkylation of an isoparaffin with an olefin which comprises in combination, alkylating an isoparaffin with an olefin in the presence of an HF acid catalyst in an alkylation operation in which an alkylation reaction zone effluent is settled to form a hydrocarbon phase and an acid phase, at least a portion of the acid phase is passed to acid rerun for removal of acid soluble oils, and another portion is recycled for reuse as catalyst, hydrocarbon phase is fractionated to produce an alkylate, saturated hydrocarbon stream containing C$_4$ hydrocarbons and a propane containing stream also containing hydrogen fluoride, water washing said propane containing stream to substantially completely remove hydrogen fluoride therefrom, drying said propane stream which now has been substantially completely freed of hydrogen fluoride by contacting said stream with solid caustic, contacting said acid soluble oil with used water wash and aqueous alkaline treating solution obtained from said water washing and from said drying, to remove from said acid soluble oil hydrogen fluoride, contacting the used treating solution upon separation from said acid soluble oil with a neutralizing agent adapted to regenerate aqueous alkaline solution and passing aqueous alkaline solution thus obtained to said alkylation operation to, therein feed olefin-containing feed fed to said operation.

2. A process according to claim 1 wherein the propane containing stream is subjected to dehydrofluorination to convert organic fluorides therein to hydrogen fluoride and olefin hydrocarbon prior to said water wash.

3. A process according to claim 1 wherein the water wash medium is steam condensate water.

4. A process according to claim 1 wherein the propane stream after water washing is contacted with solid caustic alkali to dry the same.

5. A process according to claim 4 wherein the caustic alkali is potassium hydroxide.

6. A process according to claim 1 wherein the water wash medium and aqueous alkaline solution from the drying are combined and contacted with acid soluble oil obtained from an alkylation HF rerun operation to remove from said acid soluble oil therein contained, hydrogen fluoride.

7. A process according to claim 1 wherein the aqueous alkaline solution includes potassium fluoride and is treated with a neutralizing agent such as lime adapted to regenerate aqueous alkaline solution.

8. A process according to claim 7 wherein the regenerated aqueous alkali solution is attached to an alkylation operation in which isoparaffin is alkylated with an olefin employing hydrogen fluoride catalyst and wherein the aqueous alkali solution is used to remove sulfur containing compounds from an olefin-containing feed fed to said alkylation operation.

* * * * *